United States Patent [19]

Siess et al.

[11] 4,198,849
[45] Apr. 22, 1980

[54] PYROMETRIC TEMPERATURE MEASUREMENTS IN FLAMELESS ATOMIC ABSORPTION SPECTROSCOPY

[76] Inventors: Hans Siess, Zwischen den Wegen, Owingen; Elmar Wiedeking, Am Häsle Rain 3, Sipplingen; Werner Sigle, Emerichstr. 34, Heinrich, Uberlingen, all of Fed. Rep. of Germany

[21] Appl. No.: 890,731

[22] Filed: Mar. 27, 1978

[51] Int. Cl.$^2$ .................................................. G01K 15/00
[52] U.S. Cl. .................................... 73/1 F; 73/355 EM
[58] Field of Search ............. 73/355 EM, 355 R, 1 F; 356/43, 45

[56] References Cited

U.S. PATENT DOCUMENTS

| | | | |
|---|---|---|---|
| 2,565,249 | 8/1951 | Machler | 73/355 EM |
| 3,969,943 | 7/1976 | Ohno et al. | 73/355 EM |

*Primary Examiner*—Donald O. Woodiel
*Attorney, Agent, or Firm*—S. A. Giarratana; F. L. Masselle; E. T. Grimes

[57] ABSTRACT

A method and circuitry for the pyrometric measurements of temperatures of graphite tube atomizers for flameless atomic absorption spectroscopy over very wide temperature ranges of, for example, 100° C.-2700° C. independently of the emission factors of the various graphite tubes. The heated tube is measured by a radiation pyrometer which has a very wide temperature measuring range but with an accuracy that is affected by tube emission factors and is also measured by an independent measuring system which is accurate independently of the emission factor at some particular elevated temperature. When the graphite tube reaches that elevated temperature, the output signals of both systems are mixed to produce an error signal that is used to accurately calibrate the pyrometer circuitry. Since it has been found that the percentage variation of emission factor is independent of graphite tube temperatures, the pyrometer will now produce accurate measurements over a very wide temperature range.

12 Claims, 9 Drawing Figures

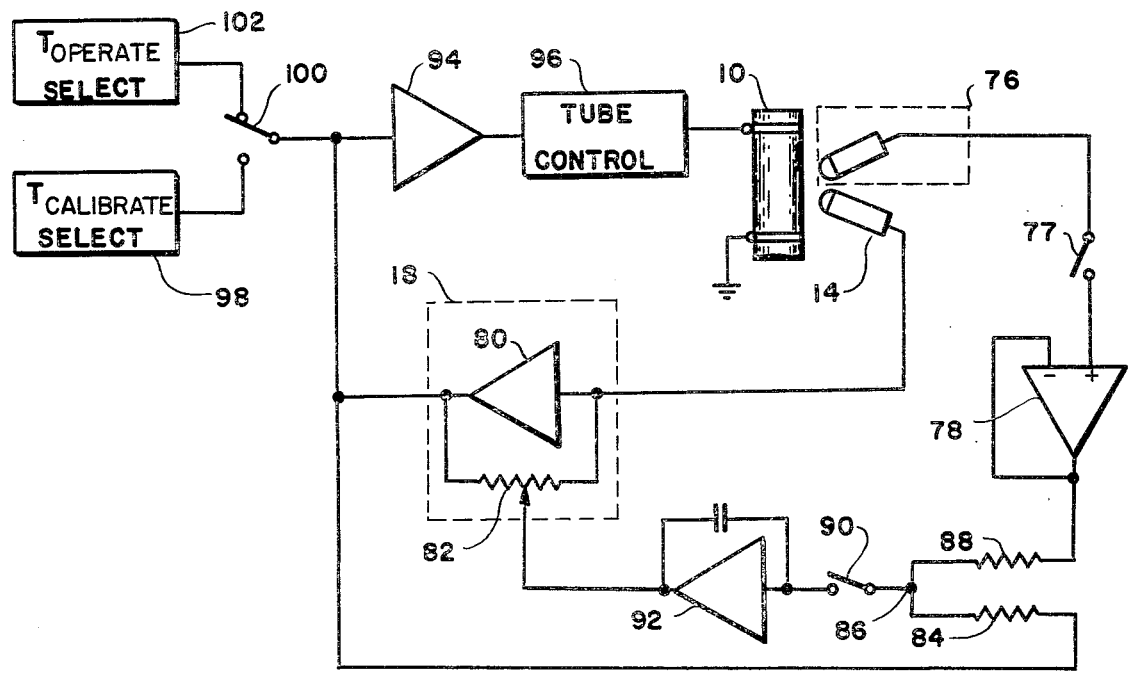
FIG. 5
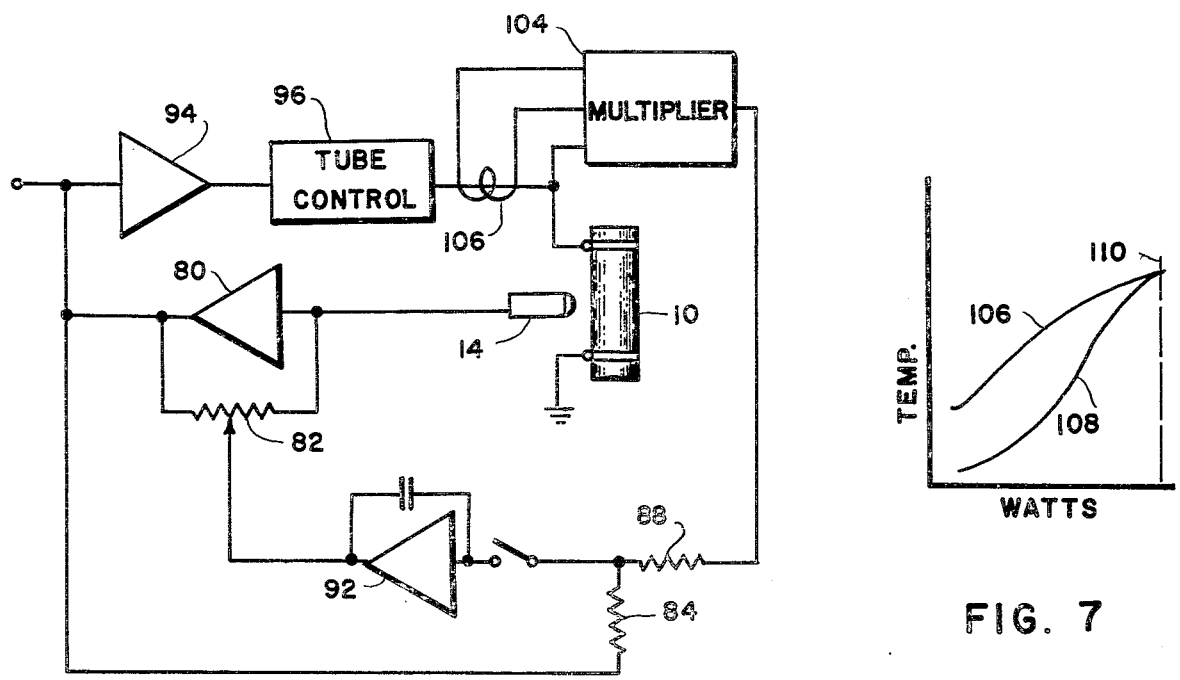
FIG. 6
FIG. 7

PYROMETRIC TEMPERATURE MEASUREMENTS IN FLAMELESS ATOMIC ABSORPTION SPECTROSCOPY

CROSS-REFERENCE TO RELATED APPLICATIONS

The invention described and claimed herein is closely related to that claimed in copending patent application, Ser. No. 805,752, filed June 13, 1977, and assigned to the assignee of this present invention. That application describes a temperature measuring system for operation in the range of approximately 100° C. to 2700° C. A measurement is made by alternately measuring the radiation emanating from the heated object and from a reference member carefully maintained at a precise predetermined temperature so that differences between the two detected values provide the signal indicative of the temperature of the object. While the invention described therein is particularly suitable for automatically controlling the temperature of a graphite tube during the drying, ashing and atomization of a sample in flameless atomic absorption spectroscopy, it has been discovered that radiation emission factor, which may vary from one graphite tube to another and which may also vary in each tube during its useful life, may produce erroneous temperature measurements unless the measuring system is carefully calibrated or all graphite tubes are carefully selected to have the same emission factor.

SUMMARY OF THE INVENTION

The pyrometric measuring system described and claimed herein is particularly suitable for automatically controlling the temperature of a graphite tube in a flameless atomic absorption spectrometer and provides a radiation pyrometer calibration that is independent of the radiation emission factor of the graphite tube.

There are methods of accurately measuring high temperature that are independent of the emission factor of the measured object. For example, accurate temperatures may be made by the use of a thermocouple, which is accurate up to approximately 600° C. but which would be destroyed at higher temperatures. Another measurement that may be made independently of the emission factor of the object is by use of a color pyrometer in which the radiation intensities of the measured object are measured in two different wavelength ranges and are correlated with each other so that the ratio of the radiation intensities in the two ranges provides the temperature measured value independent of the emission factor. A color pyrometer, however, is practical only in a relatively narrow range of high temperatures and is not adapted to cover the wide range of temperatures applied to an absorption spectroscope graphite atomizing tube, for example, 100° C. to 2800° C.

It is, therefore, the principal object of the invention to provide a method and device for the pyrometric measurement of graphite tube temperature in a flameless atomic absorption spectroscope throughout an extended temperature range of approximately 100° C. to 2800° C. independently of varying emission factors of the graphite tubes.

The invention is based upon the discovery that variations in emission factor is independent of the temperature of the graphite atomizing tube. According to the method of the invention, a graphite tube containing a suitable sample is heated to an elevated temperature that is measured by a method or device that is independent of the emission factor but which is inherently useful over a narrow temperature range. This accurately determined temperature is then used to calibrate a radiation detector that is emission factor dependent but which is useful over a very wide temperature range or approximately 100° C. to 2800° C. The circuitry of the invention samples the output signals of both the radiation detector and the calibrating means and develops an error signal for self-calibrating the radiation detector circuit, thereby correcting it for emission factor variations and rendering it accurate over its entire temperature measuring range.

DESCRIPTION OF THE DRAWINGS

In the drawings which illustrate preferred embodiments of the invention:

FIG. 5 is a block diagram illustrating a second embodiment in which the radiation detector circuit is calibrated against a color pyrometer;

FIG. 6 is a block diagram illustrating a third embodiment wherein the radiation detector is calibrated by power measuring circuitry;

FIG. 7 is a graph used in the explanation of operation of FIG. 6;

DETAILED DESCRIPTION

Figure 1:
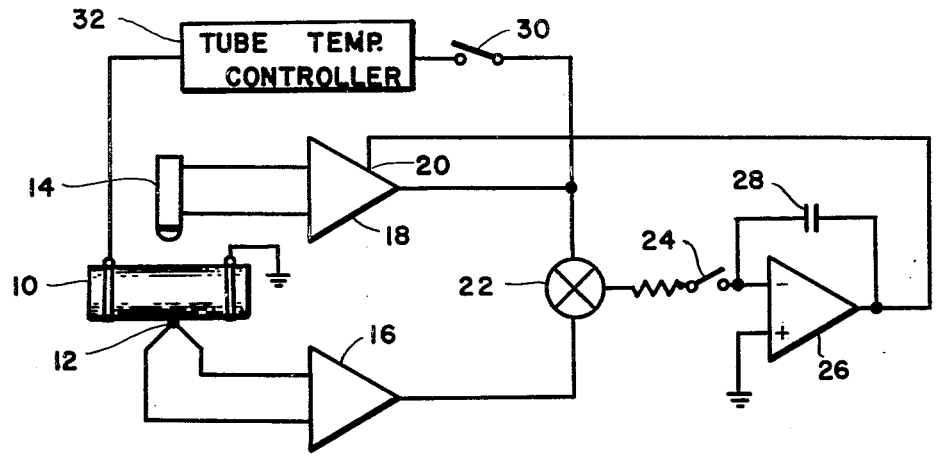
FIG. 1 is a block diagram illustrating one embodiment of the circuitry in which the radiation detector circuit is calibrated by a thermocouple circuit.

FIG. 1 is a block diagram illustrating a preferred embodiment of the invention in which the temperature of a graphite atomizer tube 10 is simultaneously sampled by a thermocouple 12 and a pyrometric radiation detector 14. Radiation detectors are capable of temperature measurements over a very wide range of, for example, 100° C. to 2800° C. but their accuracy is affected by graphite tube emission factors which vary from tube to tube, or may vary in one tube during its useful life. Thermocouples, however, are not affected by the radiation emission factor of the graphite tube, but have a very narrow useful range, normally below 600° C. Since it has been discovered that emission factor changes are independent of temperature of the graphite tube, certain types of measuring devices, such as the thermocouple 12, may be used to calibrate the radiation detector 14 to render it accurate over its wide temperature measuring range.

Accordingly, thermocouple 12 is attached to the surface of the graphite tube 10 in the conventional manner and its output voltage is applied to and amplified by amplifier 16. Simultaneously, the temperature of the tube 10 is measured by the radiation detector 14 and its output signal is applied to a variable gain amplifier 18 having a gain control input 20. The output signals from amplifiers 16 and 18 are connected in opposition at differential point 22 and the difference signal therefrom is applied through a control switch 24 to the inverting input of an integrating amplifier 26. Integrating amplifier 26 is a conventional operational amplifier having a capacitor 28 in its negative feedback circuit and has its non-inverting input coupled to ground potential. The output of amplifier 26 is coupled back to the control input 20 of the radiation detector amplifier 18.

In operation, control switch 24 is initially open and graphite tube 10 is heated to an elevated temperature which may be accurately measured by thermocouple 12. Control switch 24 is then closed and a signal representing the output differences between the thermocouple 12 and the radiation detector 14 is applied to integrating amplifier 26, resulting in an increased output voltage of that amplifier. This increased output voltage of amplifier 26 varies the gain of amplifier 18 until its output signal equals that of amplifier 16 whereupon the difference signal emanating from differential point 22 and applied to amplifier 26 becomes zero. At that point the output of the amplifier 26 remains constant whereupon the switch 24 is opened, thermocouple 12 is removed from graphite tube 10, and switch 30, in series between the output of amplifier 18 and the tube temperature controller 32, is closed. Thermocouple 12 and its associated amplifier 16 is now out of the circuitry. Integrating amplifier 26 is producing a constant voltage control of signal to the amplifier 18 and that amplifier is producing an output signal indicative of the temperature of the graphite tube and independent of the radiation emission factors of that particular tube. The temperature of graphite tube 10 may then be increased, or decreased, as desired and the detector will continue to operate accurately over its wide temperature measuring range.

Figure 2:
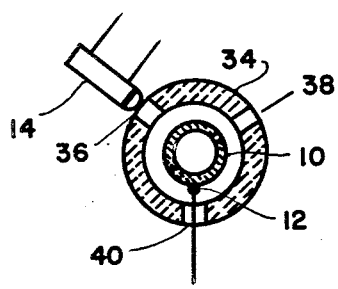
FIG. 2 is a cross-sectional view of the graphite tube illustrated in FIG. 1.

FIG. 2 is a cross-sectional drawing of tube 10 which preferably is enclosed in a casing 34 having three apertures, 36, 38 and 40. Aperture 38 is provided for admitting a sample substance into the graphite tube in a conventional manner. Aperture 36 is provided to permit observation of the tube surface by the radiation detector 14 whereby its temperature may be pyrometrically measured. The thermocouple 12 is inserted through the casing 34 through aperture 40 to be placed in contact with the graphite tube 10. When the calibrating process described above has been completed and switch 24 is opened, thermocouple 12 must be removed from the graphite tube 10 to prevent its destruction.

Figure 3:
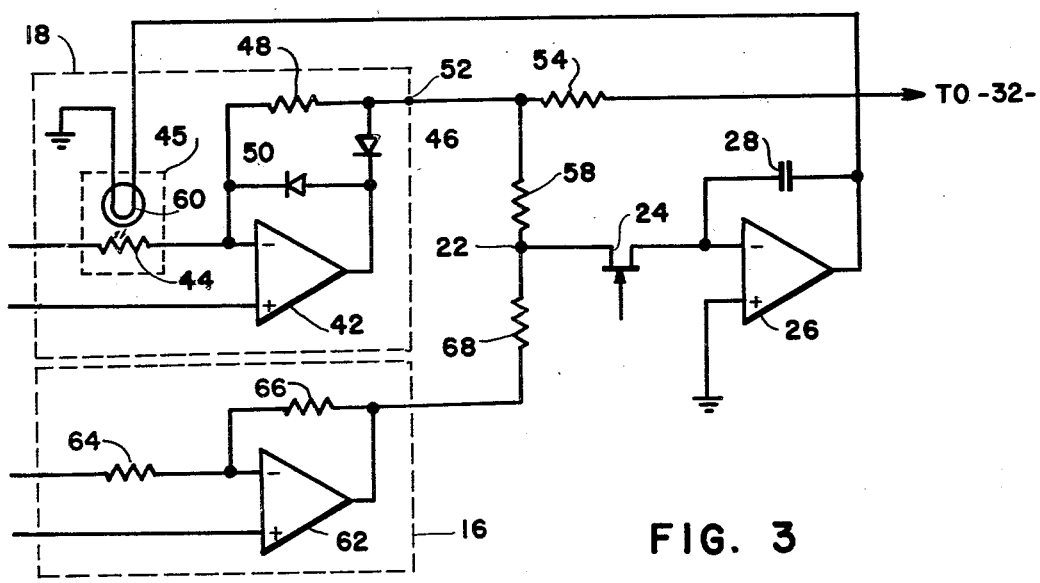
FIG. 3 is a schematic diagram illustrating in detail the circuitry of FIG. 1.

FIG. 3 is a schematic diagram illustrating the preferred embodiment of the circuitry shown in FIG. 1. As illustrated in FIG. 3, the amplifier 18, enclosed within the dashed lines, includes an operational amplifier 42, the inverting input terminal of which is coupled through the variable resistance element 44 of a raysistor 45. The output terminal of operational amplifier 42 is connected to the anode of a diode 50, the cathode of which is coupled to the inverting input terminal of amplifier 42 to provide a negative feedback loop for the amplifier. The cathode of diode 50 is also coupled through a resistor 48 to the output terminal 52 of the amplifier 18. Terminal 52 is also coupled to the anode of a diode 46, the cathode of which is coupled to the anode of diode 50 to complete the feedback circuitry. This type of negative feedback effects a desirable linearization of the amplifier output signal so that the output signal of the amplifier 18 is a linear function of the temperature of the graphite tube 10.

Output terminal 52 of amplifier 18 is connected through a resistance 54 to the tube temperature controller 32 (not shown). In addition, the output terminal 52 is connected through resistance 58 to the differential connecting point 22 and thence through control switch 24, which preferably is in the form of an FET to the inverting input terminal of amplifier 26. The output signal from the integrating amplifier 26 is applied to the light source 60 of the raysistor 45.

Amplifier 16, illustrated in FIG. 1, is represented in FIG. 3 by a dashed box and includes operational amplifier 62, which is preferably indentical with operational amplifier 42 in the amplifier 18 described above. The inverting input of operational amplifier 62 is coupled to the output of the thermocouple through a series resistance 64 and is provided with a negative loop feedback including resistor 66. The output signal from operational amplifier 62 and amplifier 16 is coupled through resistance 68 to the differential connection point 22. Resistors 58 and 68 provide a signal isolation and are preferably identical high-value resistors.

Figure 4:
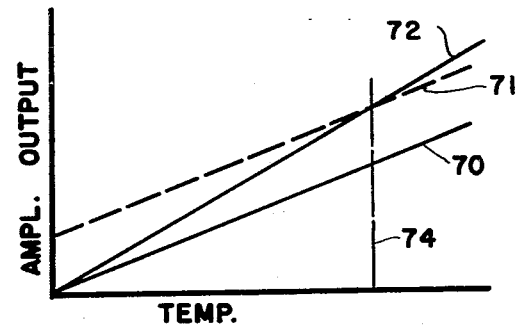
FIG. 4 is a graph for use in explaining the operation of the circuitry of FIGS. 1 and 3.

The above described negative feedback circuit in amplifier 18 insures that the output signal of amplifier 18 at terminal 52 is a linear function of temperature and is represented in FIG. 4 by the line 70. The thermocouple signal after linear amplification in amplifier 16 is also a linear function of temperature and is illustrated in FIG. 4 by the line 72. In operation, the graphite tube 10, which is monitored by both thermocouple 12 and radiation detector 14, is heated to a temperature that is within the measuring range of the thermocouple, for example, 600° C. as illustrated by the vertical dash line 74 in FIG. 4. Because of the emission factor of the graphite tube 10, the output signal represented by the line 70 is typically lower than the thermocouple output signal represented by the line 72. The voltage difference appearing at the differential point 22 of FIGS. 1 and 3 is applied to the integrating amplifier 26 through switch 24. Amplifier 26 varies the illumination of the light source 60 of the raysistor 45 until the voltage signals from amplifiers 16 and 18 become equal. This is represented by increasing the amplitude of the line 70 of FIG. 4 to its position indicated by the dashed line 71. When the voltage appearing at the differential point 22 becomes zero, the output signal from the integrating amplifier 26 will remain constant. Subsequently, the FET switch 24 is rendered non-conductive and the thermocouple 12 is removed from the graphite tube 10. The temperature of the graphite tube 10 is now under the control of the tube temperature controller 32 which receives from amplifier 18 graphite tube temperature signals that have been corrected for varying emission factors. Since emission factor variation is independent of graphite tube temperatures, the pyrometric radiation will provide accurate temperature indications for that particular graphite tube over the full temperature range.

As previously mentioned, the pyrometric radiation detector may be adjusted to correct for varying graphite tube emission factors by any high temperature measuring system that is insensitive to emission factor variations but which invariably are useful over a very narrow temperature range.

FIG. 5 is a schematic diagram of a second embodiment of the invention which employs a color pyrometer for calibration of the pyrometric radiation detector which, as previously explained, is sensitive to graphite tube emission factor variations but which, when calibrated, has a very wide useful range of between approximately 100° C. and 2800° C. In this embodiment, the graphite tube 10 is sensed by the radiation detector 14 and is also sensed by a color pyrometer 76, illustrated in FIG. 5 by the dashed box. The output signal from color pyrometer 76 is coupled to an analog value memory or sample hold circuit through a series switch 77. The sample hold circuit comprises an operational amplifier 78, the non-inverting input of which is coupled to receive the signal from switch 77. The output of amplifier 78 is coupled directly back into the inverting input and its output terminal will carry a signal representing the temperature value measured by the color pyrometer 76.

The heat radiation emanating from the graphite tube 10 is sensed by the radiation detector 14, the output of which is amplified by a variable gain amplifier 18 in a manner identical with that described in connection with FIG. 1. In the embodiment illustrated in FIG. 5, amplifier 18 includes an amplifier 80 whose gain is variable by means of a variable resistance 82, which may be a raysistor, in the negative feedback loop. The output of the amplifier 18 will carry a signal representing the actual temperature measurement made by the detector 14. Accordingly, the output of amplifier 18 is connected through a series resistance 84 to a signal differential point 86. Similarly, the value representing the temperature measurement by color pyrometer 76 and appearing at output terminal of the amplifier 78 is coupled through a resistance 88 to the signal differential point 86. Unless signal scaling is required, resistors 84 and 88 are identical in value and, since the signals applied to the point 86 are in opposition, the signal at point 86 will represent the difference in values measured by the color pyrometer 76 and the radiation detector 14. This difference value is applied through a series switch 90 and an integrating amplifier 92, the output of which is used to vary the resistance of the potentiometer 82 to the point where the output signals from amplifiers 78 and 18 are equal and the signal appearing at the differential point 86 is zero.

The output signal from amplifier 18 represents the true temperature of the graphite tube 10 as measured by the radiation detector 14 now corrected for variations in graphite tube emission factors. The output signal from amplifier 18 is therefore applied to the graphite tube controller circuit, which includes a preamplifier 94 and a tube control circuit 96 which regulates the current through the heating windings of the graphite tube 10 to acquire and maintain a selected input temperature for either calibrating a radiation detector circuit or for operation of the tube in an atomic absorption spectroscopic test.

In operation, an appropriate temperature at which color pyrometer 76 is designed to operate accurately, is entered into the calibration temperature input circuit 98 and the double-throw switch 100 is switched to permit the electrical signal generated by the circuit 98 to enter the input terminal of the preamplifier 94 where it is in electrical opposition with the output signal from amplifier 18. The switch 77 is closed while the switch 90 is opened so that the output signal from the color pyrometer 76 is stored in the memory 78. Subsequently, the temperature of the graphite tube is measured by the radiation detector 14 and an output signal is developed by the amplifier 18. When the temperature selected by circuit 98 is reached, as indicated by the radiation detector circuit, switch 90 is closed, and the integrating amplifier 92 produces a signal that varies the value of the resistance 82 to the point where the output of amplifiers 18 and 78 are equal. At this point the radiation detector is corrected for emission factor errors, switch 90 may be opened and the switch 100 is switched from the select circuit 98 to engage the operating temperature selection circuit 102 which has previously been adjusted to produce an output signal corresponding to the temperature desired for the graphite tube 10 in subsequent tests.

A third embodiment of the invention is illustrated in FIG. 6 and includes a wattmeter 104 that produces output signal voltage corresponding to the product of the voltage across the graphite tube 10 and the current therethrough as measured by a current transformer 106 coupled to the power supply conductor of the graphite tube 10. The balance of the circuitry of FIG. 6 is identical with that of FIG. 5 with corresponding elements identified by identical reference numerals, and further explanation of the circuitry of FIG. 6 is deemed unnecessary.

The operation of FIG. 6 will be explained with reference to FIG. 7, which shows the results of extensive tests of electrical power versus temperature for a great number of different graphite tubes. The curve 106 is a power-temperature curve of a graphite tube found at the maximum resistance while the curve 108 is the results of a tube found to have the lowest resistance. The characteristics of all of the graphite tubes of a particular type are located between these two borderlines. It will be noticed that the characteristics merge at a high temperature of approximately 2000° C. as indicated by the vertical dashed line 110 of FIG. 7. Therefore, the temperature at which the curves of FIG. 7 merge is an unambiguous function of the power supplied and at this temperature the power supplied to the graphite tube 10 may be converted into a signal by the multiplier 104 for calibration of the radiation detector.

Figure 8:
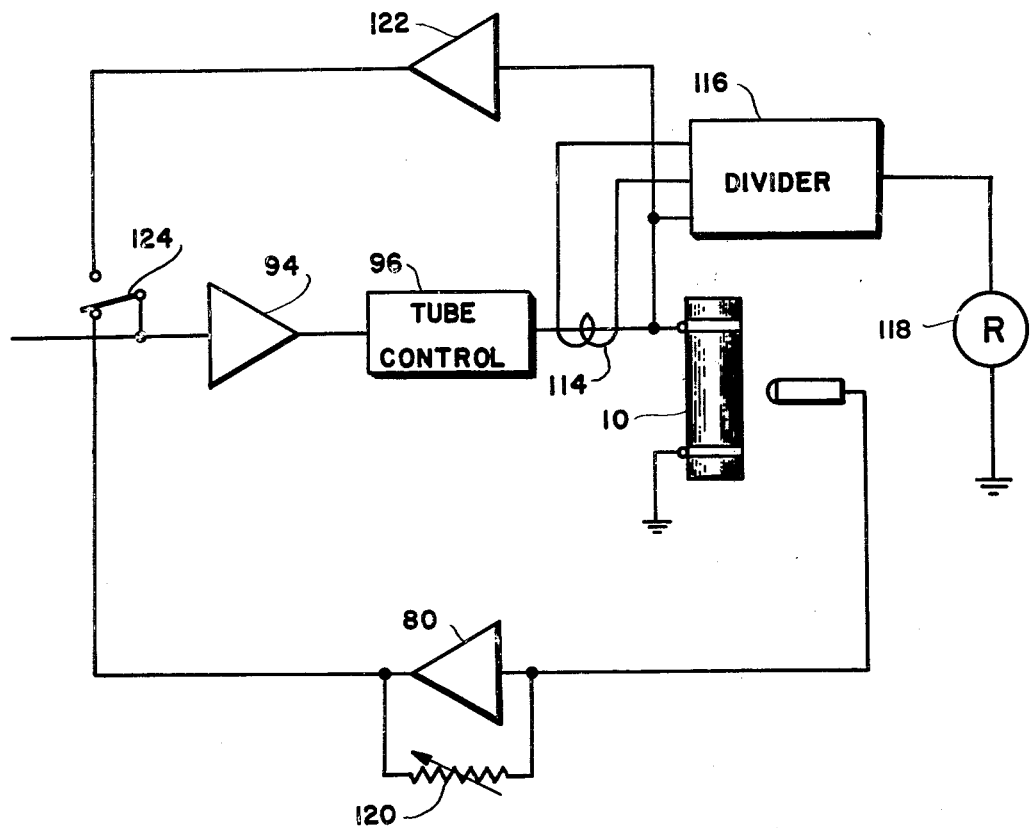
FIG. 8 is a block diagram illustrating still another embodiment of the invention.
Figure 9:
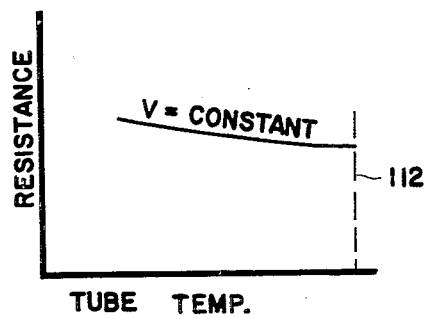
FIG. 9 is a graph used in the explanation of the circuitry of FIG. 8.

An accurate measurement of tube temperature for calibration of a radiation detector may be made by a measurement of tube resistance, as illustrated in the embodiment of FIGS. 8 and 9. As can be seen from FIG. 9, a graphite tube heated at a constant voltage attains a constant resistance at a certain relatively high temperature as indicated by the dashed line 112. Thus, that high resistance can be used to develop a signal for calibration of the radiation detector circuitry.

In FIG. 8, current through the tube heating elements is measured by a current transformer 114 and is applied to a divider circuit 116 which divides the tube voltage drop by the tube current to obtain a quotient signal proportional to the resistance of the tube. This value may be properly scaled and displayed by a resistance indicator 118 and when the measured resistance becomes constant, the value of the variable resistance 120 in the feedback circuit of the radiation detector amplifier 80 is then manually adjusted so that the output signal of the amplifier corresponds to the particular temperature represented by line 112 of FIG. 9. If desired, the voltage drop across tube 10 may be suitably amplified by amplifier 122 and introduced into the preamplifier 94 by way of a selector switch 124 so that the temperature control loop can operate as a voltage control loop to maintain a constant voltage across the tube 10.

We claim:

1. A method for adjusting the calibration of a pyrometric radiation detector affected by radiation emission factor variations and measuring the temperature of a heated object over an extended temperature range independently of the radiation emission factor variations of said object, said radiation detector being exposed to the radiation from said object and producing a detector output signal indicative of the temperature thereof to a variable gain amplifier, said method comprising the steps of:

heating the object to a predetermined temperature range within the extended temperature range of operation of said radiation detector;

measuring the temperature within said predetermined range with a second temperature measuring device that is accurate within said predetermined range independently of the emission factor of said object;

varying the gain of the variable gain amplifier to correct the value of the detector output signal, whereby said radiation detector is calibrated for temperature measurements over said extended range independently of the emission factor of said object;

heating the object to an elevated temperature above said predetermined temperature range but within the extended temperature range, and measuring the elevated temperature of the object with the radiation detector calibrated for temperature measurements independent of the emission factor of the object.

2. Circuitry for automatically adjusting the calibration of a pyrometric radiation detector for extended temperature range measurements of a heated object independently of the radiation emission factor variations of said object, said radiation detector being positioned to receive radiation from said object and producing a detector output signal indicative of the temperature thereof, said circuitry comprising:

second temperature measuring means positioned to measure the temperature of the object, said second means producing a temperature measurement within a limited temperature range independently of the emission factor of said object and generating a calibration output signal indicative of said temperature measurement;

a detector signal amplifier including a variable gain element coupled to the output of said radiation detector for amplifying the detector output signal therefrom;

differential circuitry coupled to the outputs of said second temperature measuring means and said detector signal amplifier for producing a difference signal proportional to the difference between said calibration output signal and said detector output signal; and an integrating amplifier coupled to said differential circuitry and responsive to said difference signal for adjusting said variable gain element of said detector signal amplifier to a level where said difference signal becomes zero.

3. The circuitry claimed in claim 2 wherein said second temperature measuring means comprises a thermocouple.

4. The circuitry claimed in claim 2 wherein said second temperature measuring means comprises a color pyrometer.

5. The circuitry claimed in claim 2 wherein said object is a graphite atomizing tube for use in flameless atomic absorption spectroscopy.

6. The circuitry claimed in claim 5 wherein said second temperature measuring means is a thermocouple removably positioned to sense the temperature of said graphite tube.

7. The circuitry claimed in claim 6 wherein said variable gain element of said detector signal amplifier includes a light activated variable resistance element in series between said radiation detector and said detector signal amplifier, the light source of said element being controlled by the output of said integrating amplifier.

8. The circuitry claimed in claim 5 wherein said second temperature measuring means comprises a power measuring circuit coupled to receive signal indications of voltage and current applied to said graphite tube, said power measuring circuitry producing a voltage output signal indicative of said measured power.

9. The circuitry claimed in claim 5 further including graphite tube control means for adjusting the power to said graphite tube in accordance with an input control signal.

10. The circuitry claimed in claim 9 wherein said input control signal is controlled by the output of said detector signal amplifier.

11. The circuitry claimed in claim 9 wherein said input control signal is the difference between the signal output of said detector signal amplifier and the signal output of a manually controlled temperature select circuit.

12. A method for calibrating a pyrometric radiation detector for extended temperature range measurements of an electrically heated object independently of the radiation emission factor variations of said object, said radiation detector being exposed to the radiation from said object and producing a detector output signal indicative of the temperature thereof to a variable gain amplifier, said method comprising the steps of:

determining the precise elevated temperature at which the resistance of said electrically heated object becomes constant with a constant applied heating voltage;

monitoring the resistance of the said electrically heated object until said constant resistance level is achieved; and adjusting said variable gain amplifier to produce an output signal indicative of the previously determined precise elevated temperature.

* * * * *